United States Patent [19]

Jacobi et al.

[11] 4,162,500
[45] Jul. 24, 1979

[54] RIDGED WAVEGUIDE ANTENNA SUBMERGED IN DIELECTRIC LIQUID

[75] Inventors: John H. Jacobi, Bowie; Lawrence E. Larsen, Silver Spring, both of Md.

[73] Assignee: The United States of America as represented by the Secretary of the Army, Washington, D.C.

[21] Appl. No.: 891,256

[22] Filed: Mar. 29, 1978

Related U.S. Application Data

[63] Continuation-in-part of Ser. No. 842,137, Oct. 14, 1977, Pat. No. 4,135,131.

[51] Int. Cl.² .................. G01R 27/04; H01Q 13/06
[52] U.S. Cl. ............................ 343/772; 128/653
[58] Field of Search ........... 343/719, 783, 785, 911 R; 324/58.5 A; 128/2 A

[56] References Cited

U.S. PATENT DOCUMENTS

| | | | |
|---|---|---|---|
| 2,407,690 | 9/1946 | Southworth | 343/785 |
| 3,145,382 | 8/1964 | Cuming et al. | 343/911 R |
| 3,430,249 | 2/1969 | Franks | 343/911 R |
| 4,065,772 | 12/1977 | Seavey | 343/783 |

*Primary Examiner*—Eli Lieberman
*Attorney, Agent, or Firm*—William G. Gapcynski; Werten F. W. Bellamy

[57] ABSTRACT

A system for remote microwave interrogation and imaging of biological targets comprises at least one microwave, double ridged waveguide antenna probe which operates at S-band frequencies, and a high dielectric liquid medium, preferably water, in which both the probe and the target are completely immersed. For imaging applications, the probe is positioned with respect to the target such that the target is in the near field of the antenna.

9 Claims, 2 Drawing Figures

RIDGED WAVEGUIDE ANTENNA SUBMERGED IN DIELECTRIC LIQUID

CROSS-REFERENCE TO RELATED APPLICATION

The present application is a continuation-in-part of a copending application Ser. No. 842,137, now U.S. Pat. No. 4,135,131, entitled "Microwave Time Delay Spectroscopic Methods and Apparatus for Remote Interrogation of Biological Targets," filed on Oct. 14, 1977.

FIELD OF THE INVENTION

The present invention relates generally to remote microwave interrogation and imaging of biological targets, and more particularly to interrogating and imaging systems incorporating non-contacting microwave antenna probes.

DESCRIPTION OF THE PRIOR ART AND PRIOR ART STATEMENT

Many forms of radiation have been utilized for remote interrogation and imaging of biological targets. Active imaging systems have utilized various forms of radiation, such as x-rays, radioneucliotide, heavy particle, and neutron radiation, as well as ultrasonic acoustic radiation produced by mechanical disturbances of an elastic medium. Passive imaging systems, which depend upon the Planck distribution of emitted radiation, have utilized infrared and microwave radiation for thermographic measurements. However, active imaging systems for biosystems have heretofore not been developed which utilize electromagnetic radiation in the microwave region having wavelengths greater than 3 mm. A number of factors have frustrated the development of such systems. First, at shorter wavelengths in the microwave region, where spatial resolution of an imaging system would be best, the attenuation of energy as it passes through targets having water dominated dielectrics is so great that the detection of transmitted energy is not practical and detection of reflected energy becomes increasingly more difficult the deeper is the location of the reflecting boundary within the target.

Second, although the attenuation problem can be overcome quite simply by operating at a lower frequency, the resulting increase in wavelength of the radiation requires that the physical aperture of the probe must be increased in order to efficiently radiate or receive the interrogating energy. In the case of microwave imaging systems, the use of a large aperture results in degradation of spatial resolution to the point where the system is useless.

Third, multipath propagation is a serious problem in microwave interrogation systems if measurements of transmission loss and phase shift through a lossy dielectric in a non-anechoic environment are attempted. Heretofore, useable data could not be obtained by non-invasive microwave interrogation techniques because of the multipath problem unless the probes were in contact with the target being interrogated. However, such probes suffer from a number of disadvantages. A major disadvantage is that no air gap between the probe and the target can be permitted anywhere over the surface of the probe, which limits the probes utility with respect to irregularly contoured targets. Another disadvantage is that contacting probes tend to deform the target and it is difficult to obtain uniform surface contact. A further disadvantage is that contacting probes are limited to manual scanning over complex surfaces. A still further disadvantage is that the multipath internal to the target under study is not eliminated, and the bandwidth of such probes is not wide enough to allow use of pulsed RF or Microwave Time Delay Spectroscopy techniques.

Fourth, there is a problem with the dielectric discontinuity encountered at the interface of the target surface and the environment in which it is situated. In the case of a human subject situated in free space, the difference between the dielectric constants of air and skin is such that there will be a large reflection of the incident energy at this interface.

In the probe of the present invention, the wavelength of the interrogating radiation is contracted, and the physical aperture is reduced, by completely immersing a transmitting microwave antenna, receiving antenna, and the target into a liquid medium having a high dielectric constant, such as water. It is known in the prior art to load the interior of electromagnetic antennas with a high dielectric material, either solid or liquid, in order to contract the wavelength thereof. A representative example of such antennas is disclosed in U.S. Pat. No. 974,762 (Fessenden), wherein parabolic transmitting and receiving antennas for a spark gap transmitter are filled with a liquid, such as water, having a high dielectric constant. A further example of such antennas is the contact probe for microwave interrogation of biological targets described in an article by Barrett and Myers, entitled "Subcutaneous temperatures: a method of noninvasive sensing," published in volume 190 of *Science*, pp. 669–671 (1975), wherein a rectangular waveguide antenna is interiorly filled with a plastic material containing titanium dioxide. It is to be noted that interior loading of an antenna creates an impedance mismatch at the interface with the surrounding space and results in a reduced bandwidth which becomes so severe at the S-band microwave frequencies which are used in microwave imaging systems as to prevent the use of such antennas as non-contacting probes.

Although acoustic imaging systems and sonars do not utilize electromagnetic radiation, operate at relatively low frequencies, and involve different principles of operation, it is noted that the ultrasonic transducer elements used in these acoustic imaging system are completely immersed in a water medium. An example of an acoustic imaging system is disclosed in U.S. Pat. No. 3,269,173 (von Ardenne).

There have also been several efforts in the field of communication, primarily underwater, which have utilized electromagnetic antennas completely submerged in a high dielectric medium. Generally speaking, such activity has involved low frequency radiation, much below the microwave frequencies used in microwave imaging systems, because of the attenuation problem noted above. Further, such antennas have typically been of the long wire or loop type and are not suitable for imaging applications. There also have been preliminary investigations of the suitability of dipole radiation at a frequency of 14 MHz in a water medium for communication purposes, using electrically insulated dipole antennas submerged in a lake. These activities are described in a paper by Shen, et al., "Measured field of a directional antenna submerged in a lake," *IEEE Trans. Antennas and Propagation*, Vol. AP-24, pp. 891–894 (November 1976).

Finally, very short monopole antennas have been used as invasive probes in biosystem interrogation systems, wherein the probe is inserted into the target and radio frequency measurements are obtained in the immediate vicinity of the probe. Since the probe is physically inserted into the target, useful image scans are not possible. Further, a particular probe is limited to interrogation of specific tissues since the probe impedance is affected by the tissue into which the probe is inserted. In addition, such probes are impractical for tissues having low dielectric constants, such as bone.

The prior art cited hereinabove includes, in the opinion of the applicants, the closest prior art of which they are aware. However, there is no representation that no better art exists.

SUMMARY OF THE INVENTION

These and other disadvantages of the prior art are overcome by a system constructed in accordance with the present invention for remote microwave interrogation and imaging of a biological target, which comprises at least one microwave antenna probe capable of operating at S-band frequencies, and a liquid medium having a dielectric constant greater than that of air in which both the probe and the target are completely immersed. Preferably, the liquid medium has a dielectric constant in the range of approximately 40 to 80, and advantageously may be water. In accordance with a further aspect of the invention, the probe is positioned with respect to the target such that the target is in the near field of the probe.

In accordance with another aspect of the invention, a rectangular waveguide is preferred over other configurations of the probe, and a double or quad ridged waveguide is the preferred form of rectangular waveguide, because of bandwidth considerations.

With a system constructed according to the present invention, significant improvements in the spatial resolution of near field imaging of the target are achieved. Further, there is no need to provide an anechoic chamber in which to perform interrogation or imaging of the target, since a reasonably small volume of the high dielectric medium provides sufficient attenuation of multipath radiation so as to constitute an inherently anechoic environment. Finally, when a water dielectric medium is utilized, there is improvement of energy coupling into the biological target, since the dielectric constants of external tissues such as skin are much more closely matched to water than they are to air. Also, in the case of human targets, water hydrates the corified epithelium and improves the impedance match at the 100–200 microns of the skin which would otherwise be very low in water content.

Other features and advantages of the invention will be set forth in, or apparent from, the detailed description of a preferred embodiment found hereinbelow.

DESCRIPTION OF THE PREFERRED EMBODIMENT

Figure 1:
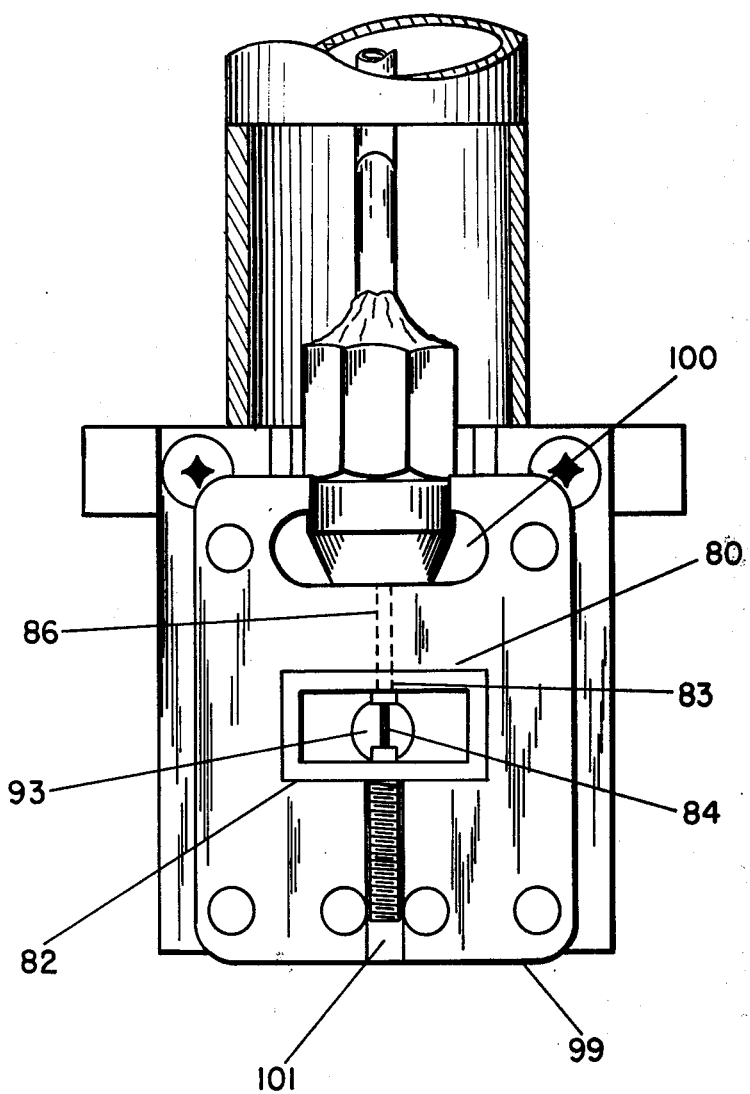
FIG. 1 is a front elevational view of a preferred probe embodiment constructed in accordance with the present invention.
Figure 2:
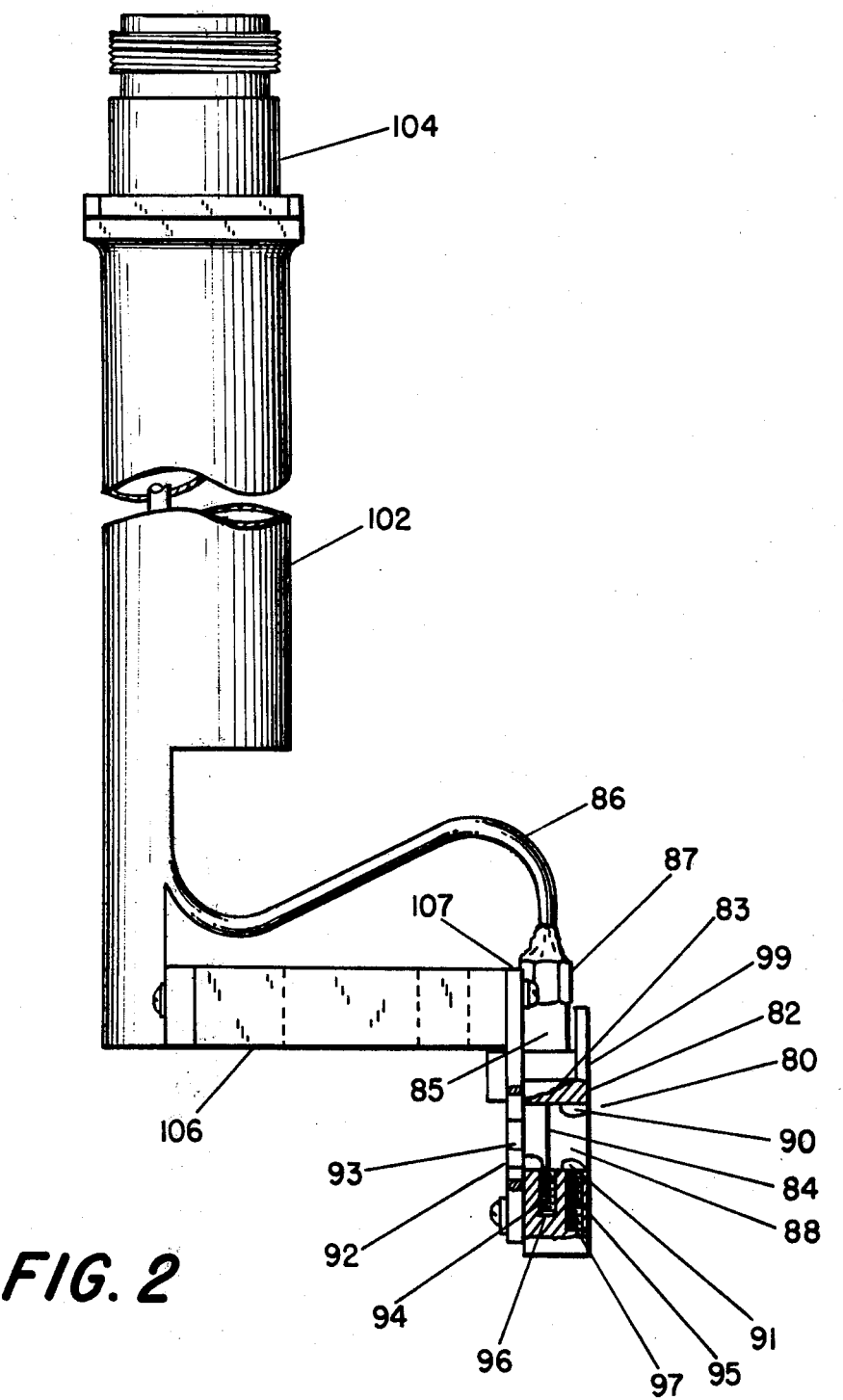
FIG. 2 is a side elevational view, partially cut away, of the probe illustrated in FIG. 1.

A preferred non-contacting probe constructed in accordance with the present invention is depicted in FIGS. 1-2. The probe, generally denoted 80, comprises a microwave antenna in the form of double ridged waveguide 82, which is approximately 6.7 mm in length and 7.7 mm in width. The length of waveguide 82 represents a compromise between internal loss and ease of impedance matching, since a shorter length, on the order of 3 mm, would be preferable from the standpoint of power loss, but would not permit the use of tuning screws for impedance matching. It is to be noted that any configuration of microwave antenna may be utilized, with a rectangular waveguide to be preferred over other forms, and a double or quad ridged waveguide to be preferred over a rectangular waveguide.

The top wall of waveguide 82 is provided with an aperture 83, through which the feed probe 84 of a standard 50 ohm impedance coaxial input cable 86 having a fluorocarbon dielectric such as "Teflon" is inserted by means of a standard female connector 85 mounted on the top surface of waveguide 82 and a standard male connector 87 mounted on the end of cable 86.

As shown, the top ridge 90 of waveguide 82 extends longitudinally along the upper interior surface only from the front end of waveguide 82 to the perimeter of aperture 83, while the bottom ridge 91 extends longitudinally along the entire lower interior surface from the front end to the rear end of waveguide 82. In addition, as shown, the front ends of both top ridge 90 and bottom ridge 91 are bevelled. Two holes 94 and 95, size 2-56, are provided in bottom ridge 91 of waveguide 82 for receiving tuning screws 96 and 97, respectively, which are used to obtain a broader impedance match. Hole 94 is substantially coaxial with aperture 83. It is noted that the rear screw 96 does not protrude into waveguide cavity 88, while front screw 97 does protrude into cavity 88.

Feed probe 84 is inserted into cavity 88 and is shorted to tuning screw 96, and thus to the bottom ridge 91 of waveguide 82 in order to control the VSWR. Preferably, probe 84 is oriented substantially perpendicularly with respect to bottom ridge 91. The diameter of probe 84 is also reduced to approximately 0.5 mm to provide a better match to the high impedance ridges of waveguide 82. Probe 80 further comprises a shorting plate 92 mounted at the rear of waveguide 82 and positioned with respect to feed probe 84 so as to obtain the smoothest impedance match over the operating bandwidth of the probe. Shorting plate 92 is provided with a 2.2 mm diameter hole 93 to facilitate removal of air bubbles trapped in waveguide 82 when antenna 80 is immersed in the dielectric medium, and to permit alignment of probe 80 with respect to the target. The dimension of hole 93 is determined by the bandwidth of the radiation to be transmitted, being sized so as to be below the cutoff frequency for the bandwidth of the radiation.

The dielectric of feed probe 84 is preferably inserted into aperture 82 such that the dielectric is approximately even with the upper interior surface of waveguide 82. Final impedance matching is obtained by simultaneous adjustment of tuning screws 96 and 97 and penetration of the dielectric into aperture 83.

Probe 80 is advantageously enclosed in a conventional double ridged waveguide flange 99, which provides mechanical stability and a means for mounting extensions onto probe 80. Preferably, flange 99 is machined with notches 100 and 101 to permit connection of feed cable 86 onto connector 85, and access to tuning screws 96 and 97.

In use, probe 80 and the associated flange 99 are advantageously mounted at the end of a hollow tube 102 which supports probe 80 and provides a conduit which protects cable 86. Cable 86 is terminated at the distal end of tube 102 in a conventional type N connector 104. To reduce the effect of reflection off tube 102, probe 80 is supported 5 cm in front of tube 102 by means of a metal standoff 106 and connector 107.

Probe 80 is designed to be operated totally immersed in a dielectric medium and have an operating bandwidth of 2000 MHz to 4000 MHz. The dimensions which have been cited hereinabove assume that the dielectric medium is water, which is preferably distilled, and at a temperature of 32° C. If a medium with a different dielectric constant is to be used, then the dimensions would need to be altered accordingly. In general, if the medium has a dielectric constant lower than that of water, larger dimensions would be required, and conversely, if the medium has a dielectric constant higher than that of water, smaller dimensions would be required.

The dielectric medium which is employed may be any high dielectric medium which is physiologically and electrically acceptable. For biological targets, media such as deuterium oxide, ethylene glycol, and methanol may advantageously be used in addition to water. In the case of biological targets having tissues with dielectric constants in the range of 5 to 80 at S-band frequencies, such as human subjects, a medium having a dielectric constant in the range of approximately 40 to 80 is preferable as providing the best impedance match to both the antenna and the target. Water is preferred because of its acceptable loss characteristics, inertness, and match to tissue, in addition to its high dielectric constant.

The volume of dielectric medium in which probe 80 and the target to be interrogated are immersed should be sufficient to constitute an anechoic environment for interrogation of the target. Satisfactory results have been achieved with a water medium contained in a tank which is 45.7 cm on a side and filled to within 6.4 cm of the top, and with probe 80 immersed 17.8 cm below the surface of the water.

The use of probe 80 as the antennas of a microwave time delay spectroscopic remote interrogation system is described in the copending application referred to hereinabove, which is hereby incorporated by reference. For microwave imaging, it is important that the target be positioned within the near field of the probe(s) which are utilized.

Tests conducted on the preferred embodiment of probe 80 described hereinabove have indicated that the maximum effective range of a probe 80 with a water dielectric is between approximately 15 to 31 cm. These tests further demonstrate that probe 80 has good impedance characteristics (VSWR less that 2.3) and reasonable losses (combined loss for two antennas less than 6 dB over almost 80% of an octave bandwidth from 2000 to 4000 MHz, and less than 14 dB total loss for both antennas at the highest frequency). The tests also demonstrate that probe 80 may be used to create line scan images of dielectric targets. Objects with a diameter of 1.8 mm and spacing of 10 mm are easily detected by interrogating radiation having a wavelength of 75 mm. The resolution of the probes 80 (in terms of separating two closely spaced objects) is between 5 and 10 mm and appears to be limited by the width of the broad dimension of the opening of waveguide 82. In addition, the tests demonstrate that all four parts of the scattering parameter data, i.e., the magnitude and phase of the reflection and transmission coefficients, must be considered in formulating an image.

Although the invention has been described with respect to an exemplary embodiment thereof, it will be understood that variations and modifications can be effected in the embodiment without departing from the scope or spirit of the invention.

We claim:

1. A system for remote microwave interrogation and imaging of a biological target comprising:
   a. at least one microwave antenna probe with a rectangular ridged waveguide having a radiating open aperture at one end which operates at S-band frequencies, and
   b. a liquid medium selected from the group consisting of water or deuterium oxide, said microwave antenna probe and the target being completely immersed in said liquid medium.

2. The system of claim 1 wherein said waveguide is a double ridged waveguide having top and bottom ridges.

3. The system of claim 2 wherein the front edges of said waveguide ridges are bevelled.

4. The system of claim 3 wherein said microwave antenna probe further comprises a feed probe, the top surface of said double ridged waveguide defines an aperture aligned with said waveguide ridges, said feed probe being inserted through said aperture into said double ridged waveguide and electrically connected to said bottom waveguide ridge so as to be substantially perpendicular thereto, the top waveguide ridge extends from the front edge of said double ridged waveguide to the periphery of said aperture, and said bottom waveguide ridge extends from the front edge to the back edge of said double ridged waveguide.

5. The system of claim 4 wherein said bottom waveguide ridge is provided with first and second tuning screws.

6. The system of claim 5 wherein said microwave antenna probe further comprises a shorting plate mounted at the rear of said double ridged waveguide and positioned with respect to said feed probe so as to optimize the impedance match over the operating bandwidth of said microwave antenna probe.

7. The system of claim 1 wherein the dielectric constant of said liquid medium is approximately 80.

8. The system of claim 7 wherein said microwave antenna probe is positioned with respect to the target such that the target is in the near field of said microwave antenna probe.

9. The system of claim 7 wherein the dielectric medium is water.

* * * * *